Figure 1A:
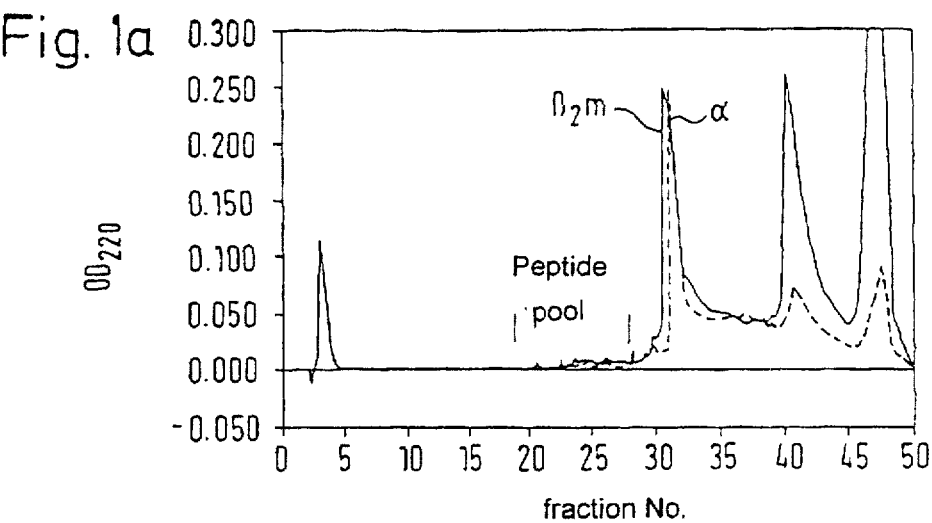

United States Patent [19]

Rammensee et al.

[11] Patent Number: 5,747,269

[45] Date of Patent: May 5, 1998

[54] DETERMINATION OF PEPTIDE MOTIFS ON MHC MOLECULES

[75] Inventors: Hans-Georg Rammensee, Tübingen, Germany; Kirsten Falk; Olaf Rötzschke, both of Sommerville, Mass.; Stefan Stevanović, Plankstadt; Günther Jung, Tübingen, both of Germany

[73] Assignee: Max-Planck-Gesellschaft zur Forderung der Wissenschaften e.V., Göttingen, Germany

[21] Appl. No.: 146,145

[22] PCT Filed: Apr. 15, 1992

[86] PCT No.: PCT/EP92/01072

§ 371 Date: May 9, 1994

§ 102(e) Date: May 9, 1994

[87] PCT Pub. No.: WO92/21033

PCT Pub. Date: Nov. 26, 1992

[30] Foreign Application Priority Data

May 17, 1991 [DE] Germany .................. 41 16 256.0

[51] Int. Cl.$^6$ .................. G01N 33/531; G01N 33/68
[52] U.S. Cl. .................. 435/7.24; 435/7.5; 436/86; 436/89; 530/344
[58] Field of Search .................. 435/7.24, 7.5; 530/868, 344, 326–328; 436/86, 89

[56] References Cited

U.S. PATENT DOCUMENTS 5,356,779  10/1994  Mozes et al. .................. 435/7.24

OTHER PUBLICATIONS

K. Falk et al, *Nature*, 351, 290–296, 1991.
D.F. Hunt et al. *Science*, 255, 1261–1263, 1992.
D.F. Hunt et al, *Science*, 256, 1817–1820, 1992.
T.S. Jardetsky et al, *Nature*, 353, 326–329, 1991.
E. Mozes et al, *Embo Jour.*, 8, 4049–4052, 1989.
O. Roetzschke et al, *Europ. Jour. Immunol.*, 21, 2891–2894, 1991.
O. Roetzschke et al, in J.A. Smith et al (EDS.), *Peptides, Chemistry and Biology*, ESCOM, 1992, pp. 832–834.
Rotzschke et al, *Nature*, 348, 252–254, 1990.
Van Bleek et al, *Nature*, 348, 213–216, 1990.

*Primary Examiner*—David Saunders
*Attorney, Agent, or Firm*—Nikaido, Marmelstein, Murray & Oram LLP

[57] ABSTRACT

The present invention concerns a method for the determination of allele-specific peptide motifs on molecules of the major histocompatibility complex (MHC) of classes I and II as well as the peptide motifs which are obtainable by the method according to the invention. In addition the use of the peptide motifs according to the invention for the production of a diagnostic or therapeutic agent is disclosed.

12 Claims, 1 Drawing Sheet

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:

(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:1:

Thr Tyr Gln Arg Thr Arg Ala Leu Val
1               5

(2) INFORMATION FOR SEQ ID NO:2:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:2:

Ser Tyr Phe Pro Glu Ile Thr His Ile
1               5

(2) INFORMATION FOR SEQ ID NO:3:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:3:

Ile Tyr Ala Thr Val Ala Gly Ser Leu
1               5

(2) INFORMATION FOR SEQ ID NO:4:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:4:

Val Tyr Gln Ile Leu Ala Ile Tyr Ala
1               5

(2) INFORMATION FOR SEQ ID NO:5:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:5:

Ile Tyr Ser Thr Val Ala Ser Ser Leu
1               5

(2) INFORMATION FOR SEQ ID NO:6:

(i) SEQUENCE CHARACTERISTICS:
(A) LENGTH: 9 amino acids
(B) TYPE: amino acid
(D) TOPOLOGY: linear (ii) MOLECULE TYPE: peptide ( x i ) SEQUENCE DESCRIPTION: SEQ ID NO:6:

Leu Tyr Gln Asn Val Gly Thr Tyr Val
1               5

( 2 ) INFORMATION FOR SEQ ID NO:7:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:7:

Arg Tyr Leu Glu Asn Gly Lys Glu Thr Leu
1               5                       10

( 2 ) INFORMATION FOR SEQ ID NO:8:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:8:

Arg Tyr Leu Lys Asn Gly Lys Glu Thr Leu
1               5                       10

( 2 ) INFORMATION FOR SEQ ID NO:9:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:9:

Lys Tyr Gln Ala Val Thr Thr Thr Leu
1               5

( 2 ) INFORMATION FOR SEQ ID NO:10:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:10:

Ser Tyr Ile Pro Ser Ala Glu Lys Ile
1               5

( 2 ) INFORMATION FOR SEQ ID NO:11:

( i ) SEQUENCE CHARACTERISTICS:
      ( A ) LENGTH: 9 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:11:

Ser Tyr Val Pro Ser Ala Glu Gln Ile
1               5

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Ala Ser Asn Glu Asn Met Glu Thr Met
    1               5

( 2 ) INFORMATION FOR SEQ ID NO:13:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Ser Gly Pro Ser Asn Thr Pro Pro Glu Ile
    1               5                     10

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

Ser Gly Val Glu Asn Pro Gly Gly Tyr Cys Leu
    1               5                      10

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Ser Ala Ile Asn Asn Tyr
    1               5

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Arg Gly Tyr Val Tyr Gln Gly Leu
    1               5

( 2 ) INFORMATION FOR SEQ ID NO:17:

( i ) SEQUENCE CHARACTERISTICS:

(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:17:

Ser Ile Ile Asn Phe Glu Lys Leu
1               5

(2) INFORMATION FOR SEQ ID NO:18:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO:18:

Ala Pro Gly Asn Tyr Pro Ala Leu
1               5

(2) INFORMATION FOR SEQ ID NO:19:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:19:

Ile Leu Lys Glu Pro Val His Gly Val
1               5

(2) INFORMATION FOR SEQ ID NO:20:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO:20:

Gly Ile Leu Gly Phe Val Phe Thr Leu
1               5

(2) INFORMATION FOR SEQ ID NO:21:

(i) SEQUENCE CHARACTERISTICS:
(A) LENGTH: 10 amino acids
(B) TYPE: amino acid
(D) TOPOLOGY: linear (ii) MOLECULE TYPE: peptide (xi) SEQUENCE DESCRIPTION: SEQ ID NO:21:

Ile Leu Gly Phe Val Phe Thr Leu Thr Val
1               5                   10

(2) INFORMATION FOR SEQ ID NO:22:

(i) SEQUENCE CHARACTERISTICS:
(A) LENGTH: 9 amino acids
(B) TYPE: amino acid
(D) TOPOLOGY: linear (ii) MOLECULE TYPE: peptide ( x i ) SEQUENCE DESCRIPTION: SEQ ID NO:22:

Phe Leu Gln Ser Arg Pro Glu Pro Thr
1               5

( 2 ) INFORMATION FOR SEQ ID NO:23:

( i ) SEQUENCE CHARACTERISTICS:
　　　　( A ) LENGTH: 7 amino acids
　　　　( B ) TYPE: amino acid
　　　　( D ) TOPOLOGY: linear ( i i ) MOLECULE TYPE: peptide ( x i ) SEQUENCE DESCRIPTION: SEQ ID NO:23:

Ala Met Gln Met Leu Lys Glu
1               5

( 2 ) INFORMATION FOR SEQ ID NO:24:

( i ) SEQUENCE CHARACTERISTICS:
　　　　( A ) LENGTH: 9 amino acids
　　　　( B ) TYPE: amino acid
　　　　( D ) TOPOLOGY: linear ( i i ) MOLECULE TYPE: peptide ( x i ) SEQUENCE DESCRIPTION: SEQ ID NO:24:

Pro Ile Ala Pro Gly Gln Met Arg Glu
1               5

( 2 ) INFORMATION FOR SEQ ID NO:25:

( i ) SEQUENCE CHARACTERISTICS:
　　　　( A ) LENGTH: 9 amino acids
　　　　( B ) TYPE: amino acid
　　　　( D ) TOPOLOGY: linear ( i i ) MOLECULE TYPE: peptide ( x i ) SEQUENCE DESCRIPTION: SEQ ID NO:25:

Gln Met Lys Asp Cys Thr Glu Arg Gln
1               5

DETERMINATION OF PEPTIDE MOTIFS ON MHC MOLECULES

DESCRIPTION

The present invention concerns a method for the determination of peptide motifs or epitopes on molecules of the major histocompatibility complex (MHC) as well as the peptide motifs which are determined by this means and their use for the production of a diagnostic or therapeutic agent.

The cytotoxic T lymphocytes (CTL) recognize antigenic peptide epitopes in association with MHC-coded molecules. This phenomenon is called MHC restriction (1–5). Crystallography of human MHC class I molecules, HLA-2 and Aw68, revealed a groove which is formed by the α1 and α2 domains of the heavy chains (3,6). It is presumed that this groove is the binding site for antigenic peptide epitopes since both crystals contained structures of peptide size which were not compatible with MHC sequences and were located at this groove (6).

It is assumed that these peptides are derived from intracellular proteins and are presented at the cell surface in order to allow the cytotoxic T lymphocytes to check the cells for abnormal properties. MHC-associated peptides which represent T cell epitopes have already been extracted from normal or virally infected cells (2,4,5,7,8). Antigens which are recognized by the MHC class II-restricted T cells can also be mimicked in a corresponding manner by artificial peptides (9) and MHC-associated antigenic peptides were eluted by MHC class II molecules (10). Due to their position at the centre of trimolecular complexes which consist of T cell receptor, peptide and MHC molecule (11), the T cell epitopes are a central point of the specific immune system and thus there is a great need to understand the rules governing their occurrence and for a method of determination (12–15).

The object according to the invention is achieved by a method for the determination of allele-specific peptide motifs on molecules of the major histocompatibility complex (MHC) of classes I or II which is characterized in that (a) a cell extract is produced by lysing cells which contain MHC molecules, (b) MHC molecules with the peptide mixtures which are located thereon are separated from the cell extract by immunoprecipitation, (c) the peptide mixtures are separated from MHC molecules and other protein components, (d) individual peptides or/and a mixture thereof are sequenced and (e) the allele-specific peptide motif is derived from the information obtained, in particular from the sequencing of a mixture or from the sequencing of a number of individual peptides.

Peptide motifs are determined by the method according to the invention which comprise the rules by which MHC molecules select and present peptides.

The method according to the invention can be carried out with MHC molecules of class I as well as with MHC molecules of class II, whereby MHC molecules of class I are preferred. $H-2K^d$, $H-K^b$, $H-2D^b$ $H-2K^k$, $H-2K^m$ or HLA-A*0201 or A*0205 molecules are particularly preferred.

When MHC molecules are immunoprecipitated by the method according to the invention, it is advantageous to use antibodies which are specific for the MHC molecules which are desired in each case. Preferred MHC class I molecules for the use according to the invention include but are not limited to the molecules A1, A2, A3, A9, A10, A11, A28, A29, Aw19, B5, B7, B8, B12 to B18, B21, B35 and B37. Preferred MHC class II molecules for the use according to the invention include but are not limited to the molecules DR1, DR2, DR3, DR4, DR5, DRw6, DR7, Dw1, Dw2 and Dw3. For the determination of $H-2K^d$ or $H-2D^b$ molecules, $K^d$-specific antibodies (25) or $D^b$-specific antibodies (26) are for example used. Monoclonal antibodies are preferably used, it is however, also possible to use an appropriately purified polyclonal antiserum. Antibodies which can be used according to the invention can be produced de novo by means of standard techniques which are well known to a person skilled in the art. Examples of antibodies which can be used in the invention include all antibodies against HLA antigens, which are mentioned in the "Catalogue of Cell Lines and Hybridomas" of the ATCC (American Type Culture Collection, 12301 Parklawn Drive, Rockville, Md. 20852) but are not limited to these. Preferred examples (in the ATCC nomenclature), include HB82, 117, 166, 54, 122, 164, 95, 120, 116, 118, 94, 152, 178, 56, 115, 157, 119, 59, 105, 165, 144, 180, 103, 110, 109, 151 and 104. All antibodies against mouse H-2 antigens mentioned in the catalogue can also be used in the invention. The immunoprecipitation is particularly preferably carried out by solid phase-bound antibodies. Solid phase-bound antibodies can be produced in a manner well known to a person skilled in the art for example by coupling the antibody to cyanogen bromide-activated Sepharose 4B (Pharmacia LKB). Other examples of solid phases to which antibodies can be bound for the use according to the invention include agarose, cellulose, Sephadex, protein-A-Sepharose and protein-G-Sepharose but are not limited to these. The preferred method of immunoprecipitation is adsorption chromatography by means of antibodies which are coupled to beads which are manufactured from cyanogen bromide-activated Sepharose 4B (see example 1).

The separation of the peptide mixtures to be determined from MHC molecules and other protein components is advantageously carried out by a chromatographic method, preferably by reverse phase HPLC. In this connection it has proven to be advantageous to carry out the separation in a trifluoroacetic acid/$H_2O$-trifluoroacetic acid/acetonitrile gradient. Other methods which can be used according to the invention to separate peptide mixtures from MHC molecules include ion exchange, gel filtration, electrofocussing, high performance capillary electrophoresis (HPCE) and gel electrophoresis but are not limited to these. Another means for carrying out the separation is ultrafiltration in which a membrane with a permeability of 3000 or 5000 or 10000 Da is used. The separation is preferably carried out by means of HPLC.

In the chromatographic separation of the peptide mixtures it is possible in some cases to isolate a single peptide species. Consequently, step (d) of the method according to the invention comprises either the sequencing of a peptide mixture by which means a consensus sequence can be determined for the peptide motifs which are located on the respective MHC molecule or/and sequencing a defined peptide.

Normal cells, tumour cells as well as cells infected by viruses or other pathogens and in vitro cultured cells of humans or animals can be used as the starting material for the determination of peptide motifs. Normal cells which can be used in the invention include but are not limited to fresh cells such as e.g. peripheral blood lymphocytes, cells of the spleen, lung, thymus or cells of another tissue which expresses MHC molecules. Tumour cell lines used in the invention include the tumour cells EL4 and P815 but are also not limited to these. Virally infected cells which can be used in the invention include but are not limited to JY cells which are human B cells transformed by the Epstein-Barr virus. The peptide motifs determined by the method according to the invention correspond to the following basic principle:

a) They have an allele-specific peptide length of 8, 9, 10, or 11 amino acids in MHC class I molecules as well as of 8 to 15 amino acids in MHC class II molecules, b) they have two anchor positions (the term "anchor position" is used when a position shows a strong signal for a single amino acid residue or when a position is occupied by a few amino acid residues with very closely related side chains) of which one anchor position is always located at the C-terminal end and is frequently aliphatic and c) the peptides are naturally presented on MHC molecules of normal, virally infected or otherwise infected cells or cells transfected with genes or coated with antigen.

The sequencing of the self-peptide mixtures from the MHC class I molecules $H2K^d$, $H2K^b$, $H2D^b$ and HLA-A2 shows a different allele-specific peptide motif in each case which is presented by each of the class I molecules. The peptides presented by $K^d$, $D^b$ and A2 are nonamers whereas the $K^b$-presented peptides are octamers and the corresponding peptide motifs contain two anchor positions which are occupied by a single amino acid residue or by a small number of amino acid residues with closely related side chains. These anchor positions are not located at the same site in the various motifs, they can for instance be at position 5 and 9 ($D^b$) or 2 and 8 ($K^d$, A2) or 5 and 8 ($K^b$). The C-terminal anchor residues of all motifs are hydrophobic amino acids. The amino acid residues which are not located at anchor positions can be quite variable; some however, are chiefly occupied by particular amino acids, for example Pro is often found at position 4 of the $K^d$ motif, Tyr at position 3 of the $K^b$ motif and hydrophobic residues are predominant at positions 3 of the $D^b$ motif and 6 of the A2 motif. A proline anchor residue was at position 2 of $H-2L^d$.

The results obtained by the method according to the invention correspond very well with the structure of the groove in MHC class I molecules found by crystallography (3,6). Different MHC class I alleles differ at this groove by the presence of different pockets which is presumably due to the fact that the pockets can accomodate different amino acids in each case. Thus the allele-specific pockets in the MHC crystals and the side chains of the allele-specific anchor residues presumably represent complementary structures.

The present invention in addition concerns the use of the peptide motifs according to the invention in a process for the production of a diagnostic or therapeutic agent. A possible area of application for the peptide motifs is the diagnostic detection of MHC molecules. Since the MHC molecules are characterized by their individual specific binding of peptides, a binding test can be carried out by means of peptides with a marker group in which for example a biotin or a fluorescent group is coupled to the peptide as the marker group. Other labels known to a person skilled in the art can also be used in the invention. These labels include, without being limited thereto, radioactive markers such as e.g. $^{131}$I, or $^{125}$I bound to the tyrosine residues of peptides or $^3$H or $^{14}$C (both of which are incorporated into the peptides during their synthesis). Binding of the labels to the peptides can be achieved according to methods well known to a person skilled in the art. The labelling is preferably carried out at non-anchor positions. The correlations between the occurrence of autoimmune diseases and the expression of MHC molecules with disease-specific peptide motifs which are found in this manner can be utilized diagnostically. Examples of in vitro diagnostic uses of the peptide sequences according to the invention include, without being limited thereto, measurement of the binding specificity of MHC molecules, correlation of the binding specificity of MHC molecules with diseases, and determination of the sequence of T cell epitopes of unknown origin by incubating suitable cells which express the MHC molecules of interest with HPLC fractions of a peptide library (mixture of peptides which fit into the motif being examined) and determining the peptides recognized by the T cell, followed by a chromatographic comparison of the natural T cell epitope with the synthetic peptide recognized as the T cell epitope (Nature 348: 252–254 (1990)).

The invention in addition concerns the use of the peptide motifs according to the invention in a process for the production of a therapeutic agent for the therapy of disturbances of the immune system or of tumour diseases. In particular the peptide motifs according to the invention can be used for intervention in autoimmune diseases (prophylaxis and therapy), for example by blocking certain MHC molecules as well as by inducing the peptide-specific non-reactivity of T cells. In addition an intervention in transplant rejections and graft-versus-host reactions is also possible in an analogous manner. In addition the peptides according to the invention can be used in vitro and in vivo for the induction or amplification or proliferation of T cells directed against tumour cells in particular for vaccination against tumour diseases and for the therapy of existing tumour diseases in which in particular the so-called graft-versus-leukemia effect (Sullivan et al., N. Engl. J. Med. 320: 828–834) can be utilized. The peptides according to the invention can also be used to amplify T cell responses towards infectious or malignant diseases by employing MHC-binding peptides in vivo which are specific for the infectious agent or for tumours. Alternatively, T cells can be obtained from animals, their number increased in vitro by using peptides and suitable growth conditions, including cytokines such as e.g. interleukin 2, interleukin 4 or interleukin 6, and subsequently returned to the patient. In addition the peptides according to the invention can be used to treat all tumours which express antigens which can be attacked by T cells including, but not being limited to, melanomas, breast cancer, tumours of viral origin such as e.g. Burkitt's lymphoma and those tumours which are caused by human papilloma virus such as cervical carcinoma and other anogenital tumours. Peptides which are derived from T cell receptor molecules or antibody molecules can also be utilized for the targetted manipulation of immunoregulatory mechanisms, in particular for the control of autoimmune diseases and transplant rejections as well as graft-versus-host reactions. In vivo uses of the proteins according to the invention for prevention include without being limited to their use as peptide vaccines against infectious or malignant diseases and use of the information compiled in this invention with regard to suitable T cell epitopes for incorporation into all other types of vaccines including recombinant vaccines (including viruses such as vaccinia or bacteria such as salmonella or mycobacteria) and proteins which have been produced by using recombinant bacteria (e.g. E. coli) or other cells, including yeast, insect, murine or human cells.

The dosage or concentrations of the peptides according to the invention can be routinely determined by a person skilled in the art. These can be expected in vivo to be in a range of 10 μg to 1 g. In vitro concentrations can be expected to be in a range of 1 femtomole to 1 micromole. The in vivo administration includes, but is not limited to, a subcutaneous, intramuscular, intraveneous, intradermal and oral route.

In the therapeutic application, a peptide which corresponds to a peptide motif according to the invention is preferably covalently linked at the N- or/and C-terminus to lipophilic or amphiphilic groups, in particular lipophilic peptide helices. An example of such a group is tripalmitoyl-S-glycerylcysteinylserylserine.

It is intended to elucidate the invention further by the following examples in conjunction with FIG. 1.

Figure 1B:
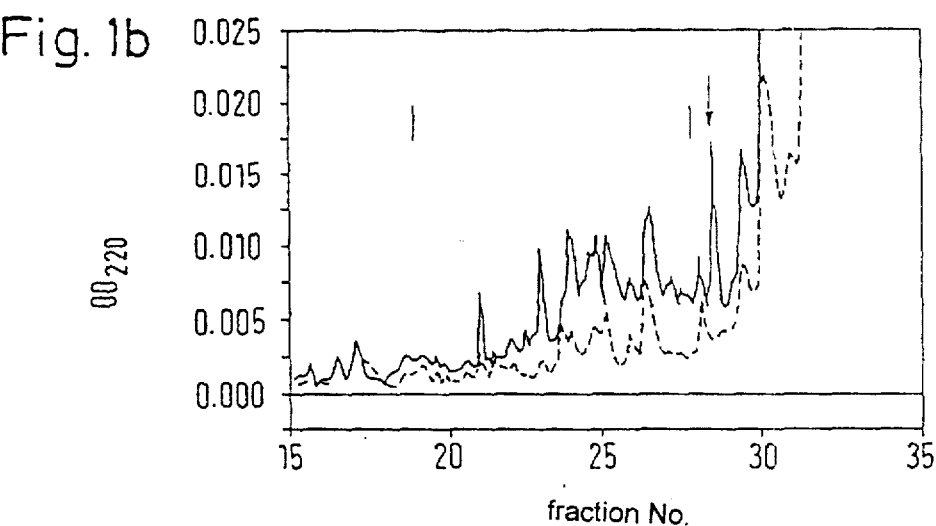
Figure 1C:
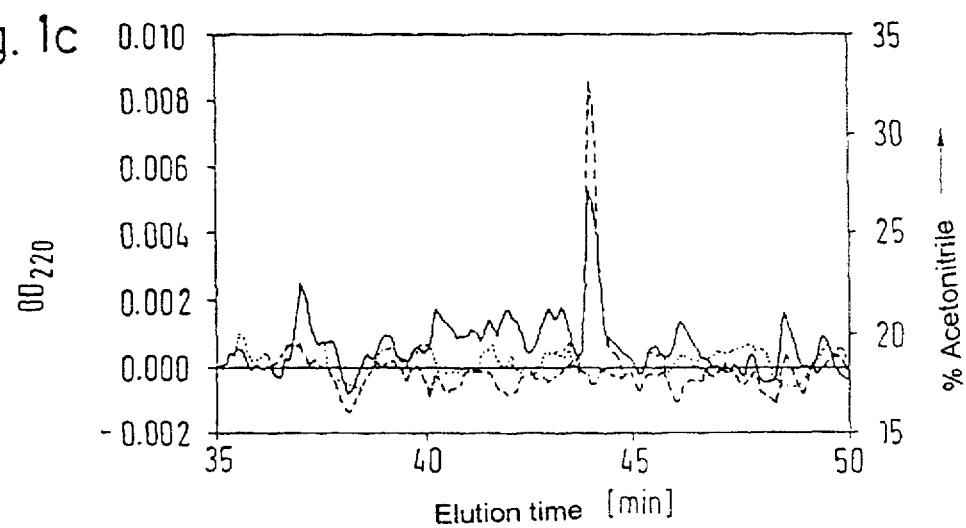

FIG. 1a shows a HPLC profile of material which was separated from P815 lysate using anti-$K^d$ antibodies, FIG. 1b shows an enlarged section from the chromatogram of 1a (fractions 15–35), FIG. 1c shows a rechromatography of the self peptide indicated by the arrow in 1b.

EXAMPLE 1

10 to 20×10$^9$ P815 tumour cells (H-2$K^d$) were pelleted and stirred for 30 minutes at 4° C. with 250 ml 0.5% Nonidet P40 in phosphate-buffered saline solution (PBS) containing 0.1 mmol/l phenylmethylsulfonyl fluoride (PMSF). The supernatant was centrifuged at 4° C. for 5 minutes at 250 g and 30 minutes at 150000 g and then passed through an arrangement for adsorption chromatography. The arrangement for adsorption chromatography consisted of three columns each with a bed volume of about 1 ml. The column material was composed of antibody-coupled or glycine-coupled beads which were produced from cyanogen bromide-activated Sepharose 4B (Pharmacia LKB) according to the protocol of the manufacturer. In each case 5 mg of $K^d$-specific antibody 20-8-4S (IgG 2a, kappa; 25) or $D^b$-specific antibodies B22-249 (IgG 2a, kappa; 26) coupled to 1 ml of the beads was used as the antibody. The supernatant of the cell extract was firstly passed through a column with glycine-coupled beads then through a corresponding column with anti-$K^d$ beads and then over anti-$D^b$ beads for a sham precipitation.

The beads were removed from all three columns and whirlimixed with 0.1% trifluoroacetic acid for 15 minutes (7). The supernatants were dried by vacuum centrifugation and separated by reverse phase HPLC using a Superpac Pep S column (C2/C18; 5 μm particles, 4.0×250 mm, Pharmacia LKB) and a Pharmacia LKB apparatus (4). Eluting agent: solution A 0.1% trifluoroacetic acid in H$_2$O (v/v), solution B 0.1% trifluoroacetic acid in acetonitrile.

The following gradient was used for the chromatographic separations shown in FIGS. 1a and b:

0 to 5 minutes, 100% A 5 to 40 minutes linear increase to 60% B, 40 to 45 minutes 60% B, 45 to 50 minutes decrease to 0% B, flow rate: 1 ml/minute, fraction size 1 ml.

The individual fractions were collected and dried by vacuum centrifugation.

FIG. 1 shows the HPLC separation of immunoprecipitated $K^d$ molecules treated with trifluoroacetic acid. FIG. 1a shows a HPLC profile of TFA-treated material which was precipitated from P815 lysate with anti-$K^d$ (continuous line) or with anti-$D^b$ (dashed line). Heterogeneous material is eluted between fractions 20 and 28 in small amounts which represents the desired allele-specific peptide mixtures.

Fractions 20 to 28 were collected from the $K^d$ preparation as well as from the sham precipitate. Both preparations were automatically sequenced using the Edman degradation method (Edman et al., Eur. J. Biochem. 1: 80–91 (1967)). The Edman degradation was carried out in a protein sequencer 477A, equipped with an on-line PTH amino acid analyzer 120A (Applied Biosystems, Foster City, Calif., 94404, USA). Glass fibre filters were coated with 1 mg BioPrene Plus and were not pre-cyclised. The sequencing was carried out using the standard programme BEGIN-1 and NORMAL-1 (Applied Biosystems). Cysteine was not modified and also could therefore not be detected.

The Edman method includes a sequential derivatization and amino acid removal starting at the N-terminus, each of which is identified by chromatography. Since it is unusual to sequence complex mixtures of peptides, the data obtained directly from the sequencing instrument are presented. Tables 1a and b show the results from two sequencing experiments for $K^d$-eluted peptides. Table 1c shows the sequencing result for a sham elution with $D^b$-specific antibodies on P815 lysates. The $K^d$-eluted peptides have a clear amino acid pattern for each position from 1 to 9 whereas the sham-eluted material has a uniform amino acid pattern throughout with a decrease in the absolute amount of each residue in each cycle. In the $K^d$-eluted peptides, only those residues which showed a more than 50% increase in their absolute amount compared to the previous cycle or the cycle before last were regarded as significant and are underlined. The first position is difficult to judge since it has no previous cycle and moreover all free amino acids present in the HPLC pool are detected at this position. The only residue at the second position whose frequency is clearly increased in comparison to the previous cycle is tyrosine (e.g. Table 1a from 60.9 pmol to 875.6 pmol). The only other residue which shows a (small) increase is phenylalanine which has a similar side chain to Tyr. This confirms the assumption which results from a comparison of the natural $K^d$-restricted influenza epitope (with the sequence TYQRTRALV (SEQ ID NO:1)) with other $K^d$-restricted peptides with regard to the tyrosine residue at position 2. In contrast there are no definite amino acid residues which are characteristic for the following positions 3 to 8. Up to 14 different residues are found at the individual positions. Ile and Leu are found at position 9. There is no increase in signal at position 10 which indicates that most of the $K^d$-bound self peptides are not longer than 9 residues. The natural $K^d$-restricted influenza peptide is thus a nonapeptide (4). The consensus sequence pattern which is derived from these results is shown in Table 1d. The most striking features are Tyr at position 2 and Ile or Leu at 9 whereas a large number of residues are found at all other positions. A comparison of this motif with peptide sequences which contain $K^d$-restricted epitopes shows that most of them match well with the $K^d$-restricted consensus monomer motif (Table 1d).

The peak in fraction 29 of FIG. 1b marked with an arrow and the corresponding fraction of the sham precipitation were chromatographed again using a higher resolution in which the fraction volume was 0.5 ml (FIG. 1c). The sharp specific peak represents a peptide with the amino acid sequence SYFPEITHI (SEQ ID NO:2) which was determined by direct sequencing. Coelution on HPLC (FIG. 1c) confirmed that this natural cell peptide is identical to the synthetic SYFPEITHI (SEQ ID NO:2) peptide. The sequence matches the consensus motif from the pool of fractions 20 to 28. (FIGS. 1a, b) which thus confirms the presence of a specific $K^d$-restricted peptide motif (Table 1d).

TABLE 1

Sequencing of the self peptide mixture which was eluted from immunoprecipitated K$^d$ molecules.

Amino acid residues (in pmol)

| Cycle | A Ala | R Arg | N Asn | D Asp | E Glu | Q Gln | G Gly | H His | I Ile | L Leu | K Lys | M Met | F Phe | P Pro | S Ser | T Thr | Y Tyr | V Val |
|---|---|---|---|---|---|---|---|---|---|---|---|---|---|---|---|---|---|---|
| (a) Experiment 1 ||||||||||||||||||
| 1 | <u>172.8</u> | 46.1 | 44.9 | 13.6 | 73.5 | 317.8 | 171.6 | 3.2 | 73.1 | 66.5 | 231.2 | 28.0 | 35.3 | 56.7 | 145.2 | 73.3 | 60.9 | 130.9 |
| 2 | 25.6 | 14.1 | 10.1 | 7.7 | 18.7 | 71.9 | 71.9 | 1.2 | 28.4 | 22.6 | 13.9 | 11.1 | <u>97.7</u> | 14.8 | 14.6 | 9.3 | <u>875.6</u> | 18.8 |
| 3 | 88.7 | 26.7 | <u>51.5</u> | 10.0 | 23.1 | 86.8 | 62.5 | <u>2.9</u> | 183.2 | 308.7 | <u>71.6</u> | <u>25.6</u> | 41.5 | 13.5 | <u>24.0</u> | <u>22.0</u> | 66.1 | <u>150.2</u> |
| 4 | <u>158.5</u> | 14.2 | 31.9 | <u>17.9</u> | <u>53.3</u> | 44.8 | 85.2 | <u>6.7</u> | 32.1 | 36.6 | 29.5 | 9.2 | 5.8 | <u>226.9</u> | <u>26.2</u> | 19.9 | 14.7 | 41.5 |
| 5 | 139.0 | 30.1 | 42.2 | <u>22.9</u> | 15.1 | 44.1 | <u>154.5</u> | 1.8 | <u>59.3</u> | <u>86.6</u> | 10.2 | <u>50.8</u> | 2.6 | 87.8 | <u>64.2</u> | <u>47.6</u> | 8.8 | <u>104.2</u> |
| 6 | 116.5 | 29.2 | 42.6 | 13.0 | 10.6 | 38.3 | 139.1 | <u>8.5</u> | <u>90.1</u> | <u>99.9</u> | <u>194.5</u> | <u>69.7</u> | <u>27.5</u> | 38.6 | 15.1 | 26.5 | <u>35.9</u> | <u>106.8</u> |
| 7 | 51.5 | 79.7 | <u>125.1</u> | <u>25.8</u> | <u>47.0</u> | <u>73.7</u> | 65.8 | 7.9 | 12.8 | 23.4 | 37.8 | 11.2 | 5.1 | 16.9 | <u>39.3</u> | <u>148.4</u> | 11.2 | 36.1 |
| 8 | 44.2 | 29.0 | 48.9 | 22.4 | <u>75.8</u> | 58.0 | 59.0 | <u>18.3</u> | 10.1 | 30.4 | 41.5 | 10.5 | <u>19.3</u> | 10.8 | 28.8 | 46.0 | <u>47.9</u> | <u>63.2</u> |
| 9 | 13.0 | 8.3 | 20.1 | 10.7 | 14.4 | 10.4 | 20.5 | 3.5 | <u>129.4</u> | <u>155.2</u> | 3.9 | 4.9 | 5.0 | 7.2 | 7.0 | 10.1 | 9.4 | 35.4 |
| 10 | 6.5 | 4.4 | 7.8 | 6.1 | 4.2 | 5.6 | 14.6 | 1.3 | 32.1 | 58.3 | 3.1 | 1.8 | 3.1 | 4.7 | 4.2 | 5.2 | 4.3 | 8.8 |
| (b) Experiment 2 ||||||||||||||||||
| 1 | 54.5 | 0.4 | 5.8 | 3.5 | 5.0 | 5.8 | 62.5 | 1.8 | 11.2 | 13.2 | 35.3 | 5.8 | 11.5 | 35.3 | 57.8 | 26.0 | 15.1 | 29.2 |
| 2 | 14.1 | 0.2 | 1.2 | 1.0 | 2.2 | 3.6 | 20.0 | 0.5 | 3.4 | 5.7 | 3.4 | 1.6 | <u>19.6</u> | 8.6 | 8.5 | 5.1 | <u>187.7</u> | 5.5 |
| 3 | <u>22.4</u> | 4.4 | <u>10.3</u> | 2.5 | <u>7.1</u> | <u>15.9</u> | 26.2 | 0.8 | <u>41.0</u> | <u>77.2</u> | <u>12.7</u> | <u>7.5</u> | <u>23.0</u> | 6.6 | 6.7 | 5.3 | 16.9 | <u>22.7</u> |
| 4 | <u>48.2</u> | 1.4 | <u>11.7</u> | <u>5.5</u> | <u>13.8</u> | 8.1 | 34.3 | <u>2.3</u> | 7.3 | 10.4 | 4.9 | 3.7 | 2.1 | <u>60.0</u> | 6.9 | 5.7 | 3.8 | 12.1 |
| 5 | 35.2 | 1.7 | 11.7 | <u>8.0</u> | 9.1 | 7.2 | <u>41.5</u> | 0.7 | <u>12.3</u> | <u>18.1</u> | 1.4 | <u>17.6</u> | 0.9 | 20.7 | <u>16.1</u> | <u>11.6</u> | 1.7 | <u>25.6</u> |
| 6 | 32.3 | <u>5.4</u> | 7.9 | 5.0 | 6.4 | 6.5 | 35.9 | 1.8 | <u>32.4</u> | <u>31.9</u> | <u>31.4</u> | <u>19.9</u> | <u>4.5</u> | 0.4 | 4.2 | 3.5 | <u>5.5</u> | <u>27.8</u> |
| 7 | 11.2 | 1.1 | <u>27.7</u> | <u>11.8</u> | <u>17.2</u> | <u>15.7</u> | 16.0 | <u>2.7</u> | 5.7 | 7.0 | 5.9 | 2.9 | 1.1 | <u>1.5</u> | <u>12.4</u> | <u>47.3</u> | 2.0 | 9.0 |
| 8 | 10.7 | <u>3.4</u> | 7.8 | 7.3 | <u>16.5</u> | 9.7 | 19.5 | <u>4.3</u> | 2.5 | 8.7 | 5.0 | 2.4 | <u>4.2</u> | 0.8 | 7.6 | 10.7 | <u>8.2</u> | <u>16.8</u> |
| 9 | 4.1 | 2.6 | 4.0 | 4.2 | 4.8 | 1.9 | 10.6 | 0.4 | <u>37.0</u> | <u>26.6</u> | 0.0 | 1.3 | 1.5 | 0.5 | 2.3 | 3.1 | 1.8 | 7.7 |
| 10 | 2.5 | 1.0 | 1.3 | 3.1 | 2.7 | 1.0 | 7.5 | 0.2 | 13.0 | 13.5 | 0.0 | 1.0 | 1.3 | 1.5 | 1.6 | 1.4 | 1.2 | 3.4 |
| (c) Sequencing of the sham precipitated material ||||||||||||||||||
| 1 | 63.5 | 5.6 | 3.6 | 3.9 | 8.3 | 11.3 | 51.5 | 2.3 | 12.2 | 16.5 | 8.4 | 3.5 | 10.8 | 47.0 | 35.2 | 27.3 | 12.7 | 24.4 |
| 2 | 24.8 | 2.5 | 3.1 | 3.6 | 7.9 | 6.2 | 33.8 | 1.3 | 6.9 | 12.1 | 4.5 | 1.4 | 5.8 | 18.4 | 7.4 | 6.4 | 6.9 | 13.8 |
| 3 | 15.2 | 0.9 | 2.5 | 3.0 | 6.6 | 3.6 | 26.6 | 1.2 | 4.1 | 11.0 | 2.7 | 1.2 | 4.2 | 16.1 | 2.7 | 4.0 | 4.3 | 8.6 |
| 4 | 11.5 | 1.0 | 2.2 | 3.2 | 5.7 | 2.6 | 19.5 | 0.8 | 3.9 | 7.3 | 2.8 | 1.1 | 2.7 | 10.7 | 1.6 | 2.4 | 3.1 | 6.4 |
| 5 | 10.5 | 1.4 | 2.1 | 3.1 | 5.0 | 2.6 | 15.7 | 1.0 | 3.1 | 6.2 | 2.3 | 0.7 | 2.2 | 7.9 | 0.9 | 1.7 | 2.6 | 5.2 |
| 6 | 8.8 | 1.1 | 1.6 | 3.1 | 4.1 | 2.0 | 12.6 | 1.1 | 2.2 | 4.6 | 1.9 | 0.6 | 1.9 | 6.5 | 1.1 | 1.4 | 1.9 | 3.9 |
| 7 | 6.8 | 1.0 | 1.6 | 2.4 | 3.5 | 1.8 | 9.8 | 0.5 | 1.8 | 3.4 | 2.1 | 0.4 | 1.7 | 4.3 | 1.6 | 1.5 | 1.7 | 2.7 |
| 8 | 0.0 | 0.3 | 0.0 | 2.1 | 0.2 | 0.8 | 0.8 | 0.6 | 1.1 | 2.8 | 1.7 | 0.3 | 1.1 | 3.6 | 0.9 | 2.2 | 0.2 | 2.6 |
| 9 | 0.1 | 0.6 | 0.0 | 1.8 | 0.0 | 0.8 | 0.7 | 0.2 | 1.6 | 2.5 | 1.7 | 0.5 | 1.1 | 3.3 | 1.3 | 1.7 | 0.1 | 2.1 |
| 10 | 0.2 | 0.3 | 0.0 | 1.7 | 0.1 | 0.5 | 0.8 | 0.2 | 1.0 | 2.5 | 1.4 | 0.3 | 1.3 | 2.7 | 0.8 | 1.7 | 0.1 | 2.1 |

TABLE 1d

The Kd-restricted peptide motif

| | Position | | | | | | | | |
|---|---|---|---|---|---|---|---|---|---|
| | 1 | 2 | 3 | 4 | 5 | 6 | 7 | 8 | 9 |
| Dominant anchor residues | | Y | | | | | | | I L |
| strong | | | | N I L | P | M | K F | T N | |
| weak | | K A R S V T | F | A H V R S F E Q K M T | A E S D H N | V N D I L S T G | H I M Y V R L | P H D E Q S | H E K V V F R |

| Known epitopes* | | | | | | | | | | Protein source | Literature reference |
|---|---|---|---|---|---|---|---|---|---|---|---|
| (SEQ ID NO: 1) | <u>T</u> | <u>Y</u> | <u>Q</u> | <u>R</u> | <u>T</u> | <u>R</u> | <u>A</u> | <u>L</u> | <u>V</u> | influenza PR8 NP 147 . 154 | 4, 29 (SEQ ID NO: 1) |

TABLE 1d-continued

The Kd-restricted peptide motif

| | | | | | | | | | | |
|---|---|---|---|---|---|---|---|---|---|---|
| (SEQ ID NO: 2) | S | Y | F | P | E | I | T | H | I | self peptide P815 |
| (SEQ ID NO: 3) | I | Y | A | T | V | A | G | S | L | influenza JAP HA 523–549 | 30, 31 |
| (SEQ ID NO: 4) | V | Y | Q | I | L | A | I | Y | A | influenza JAP HA 523 . 549 | 30, 31 |
| (SEQ ID NO: 5) | I | Y | S | T | V | A | S | S | L | influenza PR8 HA 518–528 | 32 |
| (SEQ ID NO: 6) | L | Y | Q | N | V | G | T | Y | V | influenza JAP HA 202–221 | 30, 31 |
| (SEQ ID NO: 7) | R | Y | L | E | N | G | K | E | T | L | HLA-A24 170–18233 | 33 |
| (SEQ ID NO: 8) | R | Y | L | K | N | G | K | E | T | L | HLA-Cw3 170–186 | 34 |
| (SEQ ID NO: 9) | K | Y | Q | A | V | T | T | T | L | P815 tumour antigen | 35 |
| (SEQ ID NO: 10) | S | Y | I | P | S | A | E | K | I | *Plasmodium berghei* CSP 249–260 | 36 |
| (SEQ ID NO: 11) | S | Y | V | P | S | A | E | Q | I | *Plasmodium yoeli* CSP 276–288 | 37 |

*Peptides which are known to contain $K^d$-restricted T cell epitopes were aligned with respect to their Tyr residues. Peptides which are known to be naturally processed are underlined.

EXAMPLE 2

Elution of peptides from $K^b$ and $D^b$ molecules Detergent lysates from EL4 tumour cells (H-$2^b$) were immunoprecipitated with $K^b$-specific and $D^b$-specific antibodies as described in example 1. B22-249 (see example 1) was used as the $D^b$ antibody and K9-178 (IgG 2a, K, 27) was used as the $K^b$ antibody. The peptides dissociated from MHC molecules were separated by reverse phase HPLC. $K^b$ material as well as $D^b$ material was eluted with profiles which corresponded approximately to the $K^d$ material from example 1 but, however, there were certain differences in the heterogeneous material which eluted between fractions 20 and 28.

$D^b$-restricted peptide motif

The combined fractions 20 to 28 from the $D^b$ preparation were sequenced (Table 2a, b). Positions 2 to 4 contained several residues. In contrast cycle 5 gave a strong signal for Asn. The predominant residue at position 5 of the $D^b$-eluted self peptides is thus Asn. The weak signal for Asp is caused by hydrolysis of Asn to Asp under the sequencing conditions. Positions 6 to 8 contain 5 to 14 different detectable residues. Position 9 contained a strong signal for Met, a moderate signal for Ile and a weak signal for Leu (all hydrophobic). (The significance of Met or Ile in a $D^b$-restricted epitope has already been reported, see 17). At position 10 there was no signal which indicates that $D^b$-presented self peptides are nonapeptides. The consensus motif determined from these results is shown in Table 2c. A comparison of this motif with the natural $D^b$-restricted peptide and with other peptides which contain $D^b$-restricted epitopes shows that Asn at position 5 may be an invariable anchor residue of the $D^b$-restricted peptide motif. The other residues of the $D^b$-restricted epitopes differ considerably with the exception of position 9 (with Met, Ile or Leu) which looks like a second anchor position.

TABLE 2

Sequencing of the self peptide mixture which was eluted from $D^b$ molecules

Amino acid residues (in pmol)

| Cycle | A Ala | R Arg | N Asn | D Asp | E Glu | Q Gln | G Gly | H His | I Ile | L Leu | K Lys | M Met | F Phe | P Pro | S Ser | T Thr | Y Tyr | V Val |
|---|---|---|---|---|---|---|---|---|---|---|---|---|---|---|---|---|---|---|
| (a) Experiment 1 ||||||||||||||||||
| 1 | 257.2 | 18.2 | 21.6 | 1.3 | 8.1 | 16.3 | 99.1 | 2.3 | 22.0 | 21.2 | 20.3 | 7.2 | 33.0 | 27.5 | 124.6 | 43.9 | 26.9 | 70.1 |
| 2 | 202.1 | 7.2 | 5.4 | 6.8 | 7.4 | 24.7 | 116.2 | 0.9 | 5.4 | 9.9 | 6.5 | 154.1 | 4.3 | 8.2 | 52.7 | 15.0 | 5.5 | 16.0 |
| 3 | 29.9 | 5.9 | 5.3 | 0.0 | 3.8 | 5.5 | 185.1 | 1.1 | 106.3 | 65.8 | 0.0 | 8.3 | 3.8 | 88.1 | 8.3 | 4.7 | 5.2 | 73.2 |
| 4 | 18.3 | 8.1 | 4.2 | 4.6 | 32.4 | 21.8 | 49.3 | 0.8 | 32.7 | 21.5 | 12.4 | 3.6 | 2.3 | 28.8 | 9.9 | 18.6 | 5.0 | 165.2 |
| 5 | 6.8 | 2.1 | 271.4 | 26.0 | 8.2 | 4.3 | 43.0 | 0.6 | 4.7 | 6.2 | 2.5 | 1.3 | 0.9 | 11.7 | 4.5 | 5.0 | 1.7 | 7.6 |
| 6 | 42.1 | 5.9 | 29.6 | 7.1 | 8.4 | 7.8 | 32.6 | 1.3 | 18.0 | 148.4 | 8.8 | 1.9 | 11.3 | 22.5 | 7.8 | 11.8 | 4.1 | 23.6 |
| 7 | 21.5 | 23.4 | 18.2 | 24.5 | 30.4 | 13.7 | 22.0 | 0.7 | 9.9 | 16.2 | 2.4 | 2.1 | 3.6 | 16.4 | 6.7 | 54.3 | 5.1 | 35.0 |
| 8 | 14.6 | 10.1 | 11.3 | 9.8 | 23.2 | 10.3 | 18.2 | 0.3 | 3.0 | 10.1 | 4.4 | 1.3 | 5.0 | 9.5 | 26.5 | 24.9 | 12.5 | 20.7 |
| 9 | 7.5 | 3.2 | 7.9 | 3.2 | 3.1 | 1.6 | 11.2 | 0.5 | 8.5 | 13.7 | 0.5 | 7.7 | 3.0 | 2.5 | 2.0 | 3.3 | 3.6 | 3.5 |
| 10 | 2.6 | 1.1 | 2.5 | 2.4 | 1.9 | 1.2 | 12.5 | 0.3 | 4.2 | 8.5 | 0.4 | 2.7 | 1.8 | 2.1 | 1.6 | 1.7 | 1.9 | 1.3 |
| (b) Experiment 2 ||||||||||||||||||
| 1 | 413.4 | 45.8 | 29.7 | 15.9 | 14.5 | 19.6 | 132.4 | 4.7 | 41.5 | 40.8 | 48.9 | 17.2 | 50.8 | 26.1 | 307.7 | 94.0 | 47.4 | 110.1 |
| 2 | 227.4 | 14.4 | 7.6 | 9.3 | 11.1 | 25.2 | 133.8 | 2.1 | 8.2 | 14.5 | 13.3 | 169.9 | 5.6 | 4.9 | 71.0 | 21.6 | 11.3 | 22.6 |
| 3 | 39.6 | 3.3 | 6.0 | 6.3 | 6.0 | 5.3 | 172.2 | 1.2 | 89.5 | 56.0 | 1.6 | 14.7 | 4.5 | 75.4 | 12.1 | 5.0 | 7.6 | 79.2 |
| 4 | 29.3 | 16.6 | 6.7 | 10.6 | 34.8 | 23.0 | 57.3 | 0.8 | 36.3 | 21.7 | 17.0 | 8.1 | 4.2 | 33.5 | 12.5 | 23.9 | 7.4 | 198.9 |
| 5 | 19.9 | 5.3 | 154.7 | 22.2 | 8.7 | 4.1 | 31.1 | 0.9 | 4.6 | 7.0 | 4.3 | 2.4 | 1.7 | 11.8 | 5.3 | 5.0 | 2.0 | 13.8 |
| 6 | 42.3 | 8.4 | 30.8 | 15.7 | 14.6 | 8.3 | 28.7 | 2.3 | 18.6 | 124.1 | 8.2 | 5.3 | 11.2 | 22.1 | 7.9 | 10.7 | 5.6 | 22.2 |
| 7 | 22.0 | 24.5 | 15.4 | 33.5 | 29.2 | 10.5 | 17.7 | 1.6 | 11.3 | 14.8 | 3.3 | 3.7 | 3.6 | 14.3 | 7.5 | 47.3 | 6.9 | 35.5 |
| 8 | 15.8 | 10.9 | 10.2 | 20.9 | 25.6 | 8.0 | 12.6 | 3.2 | 3.3 | 13.6 | 4.3 | 2.8 | 5.1 | 8.7 | 20.8 | 19.3 | 12.9 | 23.6 |
| 9 | 8.7 | 4.3 | 6.1 | 13.0 | 12.1 | 2.6 | 8.7 | 0.3 | 19.8 | 26.2 | 1.2 | 30.8 | 3.9 | 4.4 | 4.8 | 5.6 | 7.2 | 9.2 |
| 10 | 5.4 | 3.1 | 3.9 | 12.2 | 8.1 | 2.0 | 8.2 | 0.0 | 10.1 | 13.9 | 0.7 | 11.6 | 3.2 | 3.4 | 3.0 | 3.0 | 7.3 | 5.9 |

TABLE 2c

The $D^b$-restricted peptide motif

| | Position | | | | | | | | |
|---|---|---|---|---|---|---|---|---|---|
| | 1 | 2 | 3 | 4 | 5 | 6 | 7 | 8 | 9 |
| Dominant anchor residues | | | | | N | | | | M |
| strong | | M | I | K | | L | | | I |
| | | | L | E | | F | | | |
| | | | P | Q | | | | | |
| | | | V | V | | | | | |
| weak | A | A | G | D | | A | D | F | L |
| | N | Q | | T | | Y | E | H | |
| | I | D | | | | T | Q | K | |
| | F | | | | | V | V | S | |
| | P | | | | | M | T | Y | |
| | S | | | | | E | Y | | |
| | T | | | | | Q | | | |
| | V | | | | | H | | | |
| | | | | | | I | | | |
| | | | | | | K | | | |
| | | | | | | P | | | |
| | | | | | | S | | | |

| Known epitopes | | | | | | | | | | | Protein source | Literature reference |
|---|---|---|---|---|---|---|---|---|---|---|---|---|
| (SEQ ID NO: 12) | A | S | N | E | N | M | E | T | M | | influenza NP 366–374 154 | 4, 2 |
| (SEQ ID NO: 13) | S | G | P | S | N | T | P | P | E | I | adenovirus E1A | 38 |
| (SEQ ID NO: 14) | S | G | V | E | N | P | G | G | Y | C L | lymphocytic choriomeningitis virus GP 272–293 | 39 |
| (SEQ ID NO: 15) | S | A | I | N | N | Y | . | . | . | | simian virus 40 T 193–211 | 40 |

$K^b$-restricted peptide motif

The combined fractions 20 to 28 from the $K^b$ preparation were sequenced (Table 3a, b). Position 3 contained a strong signal for Tyr and a weak one for Pro. Position 4 showed weak signals for 5 residues. Strong signals for Phe and Tyr make both these residues predominant at position 5. The next two positions contained 5 and 3 signals respectively. Position 8 showed a strong signal for Leu, a moderate one for Met and weaker ones for Ile and Val. Position 9 showed no increase for any residue which is in agreement with the length of the known $K^b$-restricted natural peptide which is an octamer (5). An analysis of the $K^b$-restricted consensus motif and comparison with epitopes shows two anchor positions: Tyr or Phe (both with similar aromatic side chains) at position 5 and Leu, Met, Ile or Val (all with similar hydrophobic side chains) at position 8.

TABLE 3

Sequencing of the self peptide mixture eluted from $K^b$ molecules

| Cycle | A Ala | R Arg | N Asn | D Asp | E Glu | Q Gln | G Gly | H His | I Ile | L Leu | K Lys | M Met | F Phe | P Pro | S Ser | T Thr | Y Tyr | V Val |
|---|---|---|---|---|---|---|---|---|---|---|---|---|---|---|---|---|---|---|
| (a) Experiment 1 | | | | | | | | | | | | | | | | | | |
| 1 | 978.7 | 26.3 | 49.2 | 55.8 | 39.0 | 23.1 | 514.9 | 20.9 | 167.5 | 167.2 | 189.8 | 50.3 | 116.7 | 18.2 | 120.8 | 365.2 | 136.0 | 352.5 |
| 2 | 345.5 | 3.9 | 37.3 | 41.8 | 3.5 | 20.3 | 475.2 | 8.9 | 44.5 | 43.1 | 72.6 | 12.6 | 25.4 | 51.0 | 253.1 | 80.5 | 50.1 | 93.5 |
| 3 | 129.0 | 1.4 | 14.7 | 37.0 | 17.7 | 9.8 | 358.8 | 5.9 | 8.2 | 19.0 | 26.9 | 4.1 | 6.0 | 32.5 | 56.2 | 20.0 | _75.6_ | 25.9 |
| 4 | 52.1 | _3.5_ | 10.8 | 45.3 | _38.0_ | 9.2 | 246.7 | 5.0 | 4.9 | 7.0 | 17.7 | 2.4 | 1.8 | 14.6 | 23.0 | 13.4 | 12.0 | 16.4 |
| 5 | 18.9 | 1.3 | 5.5 | 34.7 | 12.0 | 3.6 | 128.2 | 2.8 | 1.9 | 4.7 | 3.8 | 1.6 | _50.5_ | 6.7 | 8.9 | 4.6 | _33.2_ | 4.9 |
| 6 | 16.2 | 0.8 | 5.6 | 32.7 | 13.0 | 3.7 | 77.9 | 2.4 | _3.1_ | 3.5 | 3.9 | 0.9 | 4.5 | 7.3 | 9.2 | _18.3_ | 7.3 | 6.2 |
| 7 | 9.9 | 0.9 | _14.9_ | 30.4 | 9.5 | _6.6_ | 51.3 | 0.6 | 0.0 | 3.4 | _9.2_ | 0.5 | 1.9 | 4.7 | 6.1 | 10.7 | 3.5 | 3.4 |
| 8 | 6.0 | 1.4 | 5.1 | 22.7 | 6.0 | 3.3 | 29.2 | 0.8 | _1.4_ | _13.5_ | 1.8 | _2.1_ | 1.0 | 3.8 | 4.1 | 3.1 | 2.5 | 3.6 |
| 9 | 4.6 | 1.5 | 2.6 | 19.9 | 4.5 | 2.3 | 21.1 | 0.9 | 0.9 | 6.9 | 1.0 | 1.5 | 1.0 | 3.0 | 3.7 | 2.2 | 1.9 | 2.1 |
| 10 | 3.9 | 0.5 | 1.9 | 17.5 | 3.7 | 2.1 | 17.5 | 1.0 | 0.5 | 4.0 | 0.8 | 0.9 | 1.2 | 2.0 | 3.5 | 1.8 | 2.8 | 1.5 |
| (b) Experiment 2 | | | | | | | | | | | | | | | | | | |
| 1 | 42.4 | 1.1 | 5.2 | 3.0 | 7.8 | 17.1 | 44.6 | 0.3 | 11.3 | 12.6 | 12.1 | 3.8 | 6.2 | 7.6 | 44.2 | 18.1 | 6.8 | 26.2 |
| 2 | 24.0 | 0.2 | _9.4_ | 2.8 | 5.1 | 8.0 | 42.5 | 0.5 | 4.7 | 6.3 | 4.0 | 1.3 | 3.7 | 3.5 | 14.9 | 10.3 | 3.1 | 6.9 |
| 3 | 10.4 | 0.3 | 2.1 | 2.6 | 3.9 | 4.0 | 25.1 | 0.7 | 2.8 | 7.9 | 2.1 | 0.9 | 3.6 | _9.8_ | 3.0 | 3.3 | _16.7_ | 10.0 |
| 4 | 9.6 | _1.3_ | 2.7 | _5.7_ | _7.5_ | 4.1 | 24.5 | 0.2 | 1.5 | 5.0 | _6.3_ | 0.7 | 1.5 | 5.9 | 3.0 | _5.9_ | 2.7 | 4.5 |
| 5 | 5.8 | 0.8 | 1.8 | 2.8 | 3.3 | 2.5 | 14.2 | 0.5 | 0.2 | 3.9 | 1.7 | 0.4 | _18.3_ | 3.5 | 1.3 | 2.0 | _20.8_ | 2.2 |
| 6 | 8.6 | 0.2 | 2.3 | 2.7 | _6.3_ | 2.7 | 9.2 | 0.0 | _1.0_ | 2.4 | 1.5 | 0.4 | 2.3 | 3.2 | _2.7_ | _5.2_ | 3.6 | 2.4 |
| 7 | 5.0 | 0.1 | _8.2_ | 3.3 | 3.9 | _4.2_ | 18.4 | 0.6 | 0.4 | 2.3 | _7.2_ | 0.1 | 1.2 | 2.1 | 1.9 | 2.8 | 1.9 | 1.2 |

TABLE 3-continued

Sequencing of the self peptide mixture eluted from K^b molecules

Amino acid residues pmol)

| Cycle | A Ala | R Arg | N Asn | D Asp | E Glu | Q Gln | G Gly | H His | I Ile | L Leu | K Lys | M Met | F Phe | P Pro | S Ser | T Thr | Y Tyr | V Val |
|---|---|---|---|---|---|---|---|---|---|---|---|---|---|---|---|---|---|---|
| 8 | 4.0 | 0.1 | 3.1 | 2.0 | 2.6 | 1.7 | 6.9 | 0.2 | 0.2 | 13.8 | 1.6 | 1.0 | 0.8 | 1.1 | 0.7 | 1.3 | 1.1 | 2.2 |
| 9 | 4.5 | 0.1 | 1.1 | 2.1 | 3.6 | 1.9 | 5.9 | 1.4 | 0.0 | 7.7 | 0.9 | 1.0 | 0.9 | 1.3 | 0.3 | 1.3 | 0.8 | 1.7 |
| 10 | 3.9 | 1.7 | 0.3 | 4.5 | 3.0 | 1.4 | 5.4 | 0.2 | 0.0 | 3.9 | 0.6 | 0.6 | 0.6 | 1.1 | 0.6 | 1.1 | 0.8 | 1.1 |

TABLE 3c

The Kb-restricted peptide motif

| | Position | | | | | | | |
|---|---|---|---|---|---|---|---|---|
| | 1 | 2 | 3 | 4 | 5 | 6 | 7 | 8 |
| Dominant anchor residues | | | | | F | | | L |
| | | | | | Y | | | |
| strong | | | Y | | | | | M |
| weak | R | N | P | R | | T | N | I |
| | I | | | D | | I | Q | V |
| | L | | | E | | E | K | |
| | S | | | K | | S | | |
| | A | | | T | | | | |

| Known epitopes | | | | | | | | Protein source | Literature reference |
|---|---|---|---|---|---|---|---|---|---|
| (SEQ ID NO: 16) R | G | Y | V | Y | Q | G | L | vesicular stomatitis virus NP 52–59 | 5 |
| (SEQ ID NO: 17) S | L | I | N | F | E | K | L | ovalbumin 258–276 | 41 |
| (SEQ ID NO: 18) A | P | G | N | Y | P | A | L | sendai virus NP 321–332 | 42 |

Example 3

HLA-A2.1-restricted peptide motif

A detergent lysate of human JY cells with the HLA-A2.1 MHC molecule (45) was immunoprecipitated with A2-specific antibodies (BB7.2, IgG2b, literature reference 28). The peptides dissociated from A2 molecules were separated by HPLC. Fractions 20 to 28 were pooled and sequenced as previously described (Table 4). The second position contained a strong signal for Leu and a moderate one for Met. 6 to 8 residues were found at each of the positions 3 to 5. Position 6 contained Val, Leu, Ile and Thr. The following two positions each showed three signals. Position 9 showed a strong Val signal and a weak Leu signal. Position 10 showed no increase for a residue which indicates that A2-restricted epitopes are nonapeptides. Leu or Met at position 2 and Val or Leu at position 9 appear to be anchor residues. Some of the known peptides with A2-restricted epitopes can be aligned with the motif, whereas this is only partially possible for others (Table 4c). The existence of several variants of A2 molecules may cause this poor correspondence of some peptides with the motif.

TABLE 4

Sequencing of the self peptide mixture which was eluted from A2.1 molecules

Amino acid residues (pmol)

| Cycle | A Ala | R Arg | N Asn | D Asp | E Glu | Q Gln | G Gly | H His | I Ile | L Leu | K Lys | M Met | F Phe | P Pro | S Ser | T Thr | Y Tyr | V Val |
|---|---|---|---|---|---|---|---|---|---|---|---|---|---|---|---|---|---|---|
| (a) Experiment 1 | | | | | | | | | | | | | | | | | | |
| 1 | 172.6 | 0.0 | 31.0 | 25.7 | 44.8 | 125.9 | 112.4 | 2.8 | 144.4 | 123.8 | 60.0 | 30.7 | 63.3 | 117.9 | 75.9 | 49.0 | 50.3 | 104.9 |
| 2 | 42.5 | 0.0 | 16.2 | 14.1 | 25.6 | 53.1 | 44.7 | 1.6 | 69.6 | 511.0 | 15.5 | 71.0 | 10.5 | 38.7 | 16.2 | 16.1 | 12.2 | 86.5 |
| 3 | 99.8 | 0.0 | 8.5 | 18.3 | 12.3 | 20.4 | 31.8 | 11.1 | 51.5 | 110.8 | 5.8 | 55.7 | 19.4 | 30.4 | 12.0 | 8.7 | 20.9 | 46.0 |
| 4 | 36.0 | 0.6 | 12.7 | 26.4 | 59.5 | 21.7 | 56.2 | 1.3 | 10.4 | 22.7 | 24.6 | 5.2 | 5.2 | 52.4 | 10.9 | 14.0 | 5.2 | 28.8 |
| 5 | 35.1 | 0.1 | 13.4 | 18.6 | 28.1 | 19.8 | 55.6 | 2.8 | 21.4 | 23.9 | 47.2 | 4.1 | 6.2 | 39.1 | 7.5 | 10.5 | 11.6 | 29.0 |
| 6 | 30.3 | 0.0 | 16.8 | 14.1 | 21.4 | 17.3 | 28.5 | 1.4 | 68.1 | 43.4 | 14.7 | 4.4 | 5.8 | 40.8 | 0.2 | 20.3 | 5.0 | 106.2 |
| 7 | 42.1 | 0.0 | 11.7 | 9.5 | 27.2 | 21.8 | 19.0 | 3.2 | 36.3 | 27.3 | 7.9 | 5.7 | 8.0 | 54.1 | 5.4 | 13.6 | 14.0 | 62.8 |
| 8 | 37.9 | 0.3 | 13.4 | 8.1 | 37.3 | 24.3 | 21.1 | 1.8 | 11.6 | 15.1 | 33.8 | 3.4 | 5.1 | 22.3 | 8.8 | 17.9 | 10.2 | 22.4 |
| 9 | 23.3 | 0.0 | 5.1 | 6.0 | 15.7 | 10.5 | 14.8 | 0.7 | 11.5 | 27.5 | 8.7 | 3.1 | 2.7 | 11.9 | 5.6 | 6.7 | 5.1 | 60.2 |

TABLE 4-continued

Sequencing of the self peptide mixture which was eluted from A2.1 molecules

| | Amino acid residues (pmol) | | | | | | | | | | | | | | | | | | |
|---|---|---|---|---|---|---|---|---|---|---|---|---|---|---|---|---|---|---|---|
| Cycle | A Ala | R Arg | N Asn | D Asp | E Glu | Q Gln | G Gly | H His | I Ile | L Leu | K Lys | M Met | F Phe | P Pro | S Ser | T Thr | Y Tyr | V Val |
| 10 | 12.0 | 0.7 | 2.6 | 4.4 | 6.5 | 5.2 | 10.2 | 0.4 | 4.5 | 12.1 | 4.5 | 1.0 | 1.8 | 7.1 | 2.7 | 3.2 | 2.3 | 20.4 |
| (b) Experiment 2 | | | | | | | | | | | | | | | | | | |
| 1 | 110.8 | 10.8 | 4.0 | 3.1 | 10.0 | 14.5 | 55.7 | 0.2 | 60.3 | 44.4 | 10.8 | 8.2 | 37.5 | 20.3 | 27.4 | 14.6 | 19.8 | 48.0 |
| 2 | 13.4 | 1.6 | 2.0 | 1.9 | 6.8 | 11.0 | 9.0 | 0.0 | 37.9 | _302.7_ | 0.0 | _26.2_ | 5.0 | 6.3 | 4.4 | 4.5 | 3.3 | 26.5 |
| 3 | _62.4_ | _3.5_ | _5.0_ | _0.1_ | 4.9 | 10.0 | 12.6 | 0.1 | 35.7 | 71.5 | 0.0 | 24.5 | _13.8_ | _13.4_ | _8.9_ | 4.8 | _17.9_ | 19.6 |
| 4 | 16.9 | 2.2 | 4.9 | 8.0 | _25.3_ | 7.9 | _24.5_ | 0.1 | 6.2 | 10.3 | _2.8_ | 1.3 | 2.0 | _22.1_ | 4.9 | 5.0 | 1.8 | 9.6 |
| 5 | 22.3 | 1.6 | _6.8_ | 8.6 | 14.3 | 9.9 | _31.8_ | 0.0 | _16.6_ | 15.1 | _8.2_ | 1.9 | _4.0_ | 16.3 | 4.5 | 4.6 | _5.7_ | _18.3_ |
| 6 | 10.6 | 1.3 | 6.6 | 3.6 | 6.4 | 6.2 | 10.1 | 0.1 | _38.7_ | _27.1_ | 0.0 | 1.4 | 2.7 | 12.6 | 3.2 | 6.1 | 1.3 | _39.2_ |
| 7 | _19.2_ | 1.0 | 4.7 | 2.5 | 7.2 | 8.0 | 5.6 | 0.2 | 22.3 | 16.1 | 0.0 | 1.9 | 3.9 | 17.4 | 1.8 | 3.5 | _3.6_ | 27.2 |
| 8 | 13.4 | 1.2 | 3.1 | 1.3 | 7.9 | 6.3 | 6.9 | 0.3 | 4.7 | 6.7 | _3.0_ | 0.6 | 2.0 | 5.1 | 2.2 | 4.9 | 1.6 | 5.3 |
| 9 | 5.7 | 0.5 | 0.9 | 0.8 | 2.9 | 2.0 | 2.7 | 0.2 | 3.8 | _11.5_ | 0.4 | 0.3 | 0.6 | 2.0 | 1.0 | 1.1 | 0.4 | _10.8_ |
| 10 | 2.9 | 0.6 | 0.5 | 0.5 | 1.0 | 0.9 | 1.8 | 0.3 | 1.6 | 5.1 | 0.4 | 0.3 | 0.3 | 0.8 | 0.4 | 0.3 | 0.2 | 3.6 |

TABLE 4c

The HLA-A2.1-restricted peptide motif (HLA-A*0201)

| | Position | | | | | | | | |
|---|---|---|---|---|---|---|---|---|---|
| | 1 | 2 | 3 | 4 | 5 | 6 | 7 | 8 | 9 |
| Dominant anchor residues strong | | L M | | E K | | V | | K | V |
| weak | I L F K M Y V | | A Y F P M S R | G P D T | I K Y N G F V H | I L T H | A Y S | E S | L |

| Known epitopes | | | | | | | | | | Protein source | Literature reference |
|---|---|---|---|---|---|---|---|---|---|---|---|
| (SEQ ID NO: 19) | I | L | K | E | P | V | H | G | V | HIV reverse transcriptase 461–485 | 43 |
| (SEQ ID NO: 20) | G | I | L | G | F | V | F | T | L | influenza matrix protein 57–68 | 44 |
| (SEQ ID NO: 21) | I | L | G | F | V | F | T | L | T V | influenza matrix protein 57–68 | 44 |
| (SEQ ID NO: 22) | F | L | Q | S | R | P | E | P | T | HIV Gag protein 446–460 | 46 |
| (SEQ ID NO: 23) | A | M | Q | M | L | K | E | . | . | HIV Gag protein 193–203 | 46 |
| (SEQ ID NO: 24) | P | I | A | P | G | Q | M | R | E | HIV Gag protein 219–233 | 46 |
| (SEQ ID NO: 25) | Q | M | K | D | C | T | E | R | Q | HIV Gag protein 418–443 | 46 |

TABLE 5

The HLA-A*0205-restricted peptide motif

| | Position | | | | | | | | |
|---|---|---|---|---|---|---|---|---|---|
| a) A*0205 | 1 | 2 | 3 | 4 | 5 | 6 | 7 | 8 | 9 |
| Dominant anchor residues | | | | | | | | | L |
| others | | V L I Q M | Y P F I N | G E D K I | V Y L T A R | I V | Q | K | |

TABLE 6

The H-2K$^k$-restricted peptide motif

| | Position | | | | | | | |
|---|---|---|---|---|---|---|---|---|
| | 1 | 2 | 3 | 4 | 5 | 6 | 7 | 8 |
| Dominant anchor residues strong | | E | K N Y M | | | | | I |
| weak | V F | | Q I L F P H | L A G P T V F | N K H | T | | |

TABLE 6-continued

The H-2K$^k$-restricted peptide motif

| | | | Position | | | | |
|---|---|---|---|---|---|---|---|
| 1 | 2 | 3 | 4 | 5 | 6 | 7 | 8 |
| | | T | | S | | | |

TABLE 7

The H-2K$^{km}$-restricted peptide motif

| | | | Position | | | | |
|---|---|---|---|---|---|---|---|
| | 1 | 2 | 3 | 4 | 5 | 6 | 7 | 8 |
| Dominant anchor residues | | | | | | | | I |
| strong | | E | K | | | | | |
| weak | | Q | N | P | A | | R | |
| | | G | Q | | R | | Y | |
| | | P | G | | K | | | |
| | | | M | | | | | |
| | | | P | | | | | |
| | | | Y | | | | | |

Literature references

1. Zinkernagel, R.M. & Doherty, P.C., Nature 248, 701–702 (1974).
2. Townsend, A.R. et al., Cell 44, 959–968 (1986).
3. Bjorkman, P.J. et al., Nature 329, 512–518 (1987).
4. Rötzschke, O. et al., Nature 348, 252–254 (1990).
5. VanBleck, G. M. & Nathenson, S. G., Nature 348, 213–216 (1990)).
6. Garrett, T. P. J., Saper, M. A., Bjorkman, P. J., Strominger, J. L. & Wiley, D. C., Nature 343, 692–696 (1989).
7. Rötzschke, O., Falk, K., Wallny, H.-J., Faath, S. & Rammensee, H.-G. Science 249, 283–287 (1990).
8. Falk, K., Rötzschke, O. & Rammensee, H.-G., Nature 348, 248–251 (1990).
9. Shimorkevitz, R., Kappler, J., Marrack, P. & Grey H., J.exp.Med. 158, 303–316 (1983).
10. Demotz, S., Grey, H. M., Appella, E. & Sette, A., Nature 343, 682–684 (1989).
11. Bjorkman, P. J. et al., Nature 329, 506–512 (1987).
12. DeLisi, C. & Berzolsky, J. A., Proc.Natn.Acad.Sci.USA 82, 7048–7052 (1985).
13. Rothbard, J. B. & Taylor, W. R., EMBO J. 7, 93–100 (1988).
14. Cornette, J. L., Margaht, H., DeLisi, C. & Berzolsky, J. A., Meth.Enzym 178, 611–633 (1989).
15. Sette, A. et al., Proc.natn.Acad.Sci.USA86, 3296–3300 (1989).
16. Maryanski, J. L., Verdini, A. S., Weber, P. C., Salemme, F. R. & Corradin, G., Cell 60, 63–72 (1990).
17. Bastin, J., Rothbard, J. Davey, J. Jones, I. & Townsend, A., J.exp.Med. 165, 1508–1523 (1987).
18. Bjorkman, P. J. & Davis, M. M., Cold Spring Harb..Symp. quant.Biol. 54, 365–374 (1989).
19. Boulliot, M. et al., Nature 339, 473–475 (1989).
20. Frelinger, J. A., Gotch, F. M., Zweerink, H., Wain, E. & McMichael, A. J., J.exp.Med. 172, 827–834 (1990).
21. Schild, H., Rötzschke, O., Kalbacher, H. & Rammensee, H.-G., Science 247, 1587–1589 (1990).
22. Townsend, AQ. et al., Nature 340, 443–448 (1989).
23. Elliott, T., Townsend, A. & Cerundolo, V., Nature 348, 195–197 (1990).
24. Cerundolo, V. et al., Nature 345, 449–452 (1990).
25. Rüsch, E., Kuon, W. & Hämmerling, G., J.Trans.Proc. 15, 2093–2096 (1983).
26. Lembke, H., Hämmerling, G. J. & Hämmerling U., Immunol.Rev. 47, 175–206 (1979).
27. Ozato, K. & Sachs, D. H., J.Immun. 126, 317–321 (1981).
28. Parham, P. & Brodsky, F. M., Hum.Immun. 3, 277–299 (1981).
29. Taylor, P. M., Davey, J., Howland, K., Rothbard, J. B. & Askonas, B. A., Immunogenetics 26, 267–272 (1987).
30. Braciale, T. J. et al., J.exp.Med. 166, 678–692 (1987).
31. Braciale, T. J., Sweetser, M. T., Morrison, L. A., Kittlesen, D. J. & Braciale, V. L., Proc.natn.Acad..Sci.USA 86, 277–281 (1989).
32. Kuwano, K., Braciale, T. J. & Ennis, F. A., FASEB J. 2, 2221 (1988).
33. Maryanski, J. L., Pala, P., Cerottini, J. C. & Corradin, G. J., J.Exp.Med. 167, 1391–1405 (1988).
34. Maryanski, J. L., Pala, P., Corradin, G., Jordan, B. R. & Cerottini, J. C., Nature 324, 578–579 (1986).
35. Sibille, C. et al., J.exp.Med.172, 35–45 (1990).
36. Romero, P. et al., Nature 341, 323–326 (1989).
37. Weiss, W. R. et al., J.exp.Med. 171, 763–773 (1990).
38. Kast, W. M. et al., Cell 59, 603–614 (1989).
39. Oldstone, M. B. A., Whitton, J. L., Lewicki, H. & Tishon, A., J.exp.Med. 168, 559–570 (1988).
40. Tevethiak S. S. et al., J.Virol. 64, 1192–1200 (1990).
41. Carbone, F. R. & Bevan, M. J., J.exp.Med. 169, 603–612 (1989).
42. Schumacher, T. N. M. et al., Cell 62, 563–567 (1990).
43. Walker, B. D. et al., Proc.natn.Acad.Sci.USA 86, 9514–9518 (1989).
44. Gotch, F., McMichael, A. & Rothbard, J., J.exp.Med. 168, 2045–2057 (1988).
45. Santos-Aguado, J., Commins, M. A. V., Mentzer, S. J., Burakoff, S. J. & Strominger, J. L., Proc.natn.Acad..Sci.USA 86, 8936–8940 (1989).
46. Clavene, J. M. et al., Eur.J.Immun. 18, 1547–1553 (1988).
47. Falk, K. et al., J.exp.Med.A4, 425–434 (1991).

We claim:

1. A method for the determination of allele-specific peptide motifs on molecules of the major histocompatibility complex (MHC) os classes I or II, comprising the steps of:
　a) lysing cells which contain MHC molecules to produce a cell extract,
　b) separating the MHC molecules on which peptide mixtures are located from the cell extract by immunoprecipitation,
　c) separating a peptide mixture from the MHC molecules or other protein components,
　d) sequencing the resulting peptide mixture, and
　e) deriving the allele-specific peptide motif from the sequencing of the peptide mixture.

2. The method according to claim 1, wherein a single peptide species is isolated in step c) and sequenced in step d).

3. The method according to claim 1, wherein the MHC molecules are class I MHC molecules.

4. The method according to claim 3, wherein the MHC molecules are selected from the group consisting of H-2K$^d$, H-K$^b$, H-2D$^b$, H-2K$^k$, H-2K$^m$, HLA-A*0201 and A*0205 molecules.

5. The method according to claim 1, wherein antibodies which are specific for a desired MHC molecule are used for the immunoprecipitation.

6. The method according to claim 5, wherein said antibodies are bound to a solid phase.

7. The method according to claim 1, wherein the separation of the peptide or peptide mixtures from the MHC molecules and other protein components is achieved by chromatography.

8. The method according to claim 7, wherein said chromatography is reverse phase HPLC.

9. The method according to claim 8, wherein the chromatography is carried out with a trifluoroacetic acid/H$_2$O-trifluoroacetic acid/acetonitrile gradient.

10. A method for producing a diagnostic agent for detecting MHC molecules, comprising the steps of:
　a) lysing cells which contain MHC molecules to produce a cell extract,
　b) separating the MHC molecules on which peptide mixtures are located from the cell extract by immunoprecipitation, c) separating a peptide mixture from the MHC molecules or other protein components, d) sequencing the resulting peptide mixture, e) deriving the alele-specific peptide motif from the sequencing of the peptide mixture, and f) preparing a diagnostic agent based on the derived allele-specific peptide motif obtained in step e).

11. The method according to claim 10, further comprising coupling said peptide motif to a marker group.

12. The process according to claim 11, wherein said marker group is a biotin or fluorescent group.

* * * * *

UNITED STATES PATENT AND TRADEMARK OFFICE
CERTIFICATE OF CORRECTION

PATENT NO. : 5,747,269

DATED : May 5, 1998

INVENTOR(S) : Rammensee et al.

It is certified that error appears in the above-identified patent and that said Letters Patent is hereby corrected as shown below:

```
Title page,
Item [22], please delete "Apr. 15, 1992" insert therefor --
```
May 15, 1992 --

Signed and Sealed this

Thirtieth Day of June, 1998

Attest:

BRUCE LEHMAN

*Attesting Officer*          *Commissioner of Patents and Trademarks*